United States Patent [19]

Brodsky

[11] Patent Number: 4,543,100
[45] Date of Patent: Sep. 24, 1985

[54] CATHETER AND DRAIN TUBE RETAINER

[76] Inventor: Stuart A. Brodsky, 690 Blackhawk Rd., NE., Albuquerque, N. Mex. 87122

[21] Appl. No.: 547,634

[22] Filed: Nov. 1, 1983

[51] Int. Cl.$^4$ ............................................. A61M 25/02
[52] U.S. Cl. ............................ 604/180; 128/DIG. 26
[58] Field of Search ............... 604/180, 174, 278, 178, 604/179; 128/DIG. 26

[56] References Cited

U.S. PATENT DOCUMENTS

| | | | |
|---|---|---|---|
| 3,138,158 | 6/1964 | Gordon et al. | 604/180 X |
| 4,040,427 | 8/1977 | Winnie | 604/180 |
| 4,221,215 | 9/1980 | Mandelbaum | 128/DIG. 26 X |
| 4,397,641 | 8/1983 | Jacobs | 604/180 |

*Primary Examiner*—Stephen C. Pellegrino
*Attorney, Agent, or Firm*—Harvey B. Jacobson

[57] ABSTRACT

A body constructed of resilient shape retentive material is provided and includes a peripheral frame of a first thickness and a membrane extending across the interior of the frame. The membrane is of a second thickness considerably less than the first thickness. The membrane includes a central opening therein and generally radial slots formed therein and extending outwardly from the opening toward the peripheral frame. Those portions of the membrane disposed between adjacent slots define generally triangular tongue portions. One side of the peripheral frame includes attaching structure in the form of pressure sensitive adhesive whereby the frame may be adhesively secured in overlying relation to the outer surface of the body skin portion. The opening may be used to receive a catheter or drain tube therethrough of a diameter greater than the diameter of the opening and with the free ends of the tongue portions disposed about the opening laterally deflected out of the plane of the remainder of the membrane and frictionally engaged with the catheter or drain tube. In this manner, the catheter or drain tube is frictionally retained against longitudinal shifting relative to the body.

5 Claims, 4 Drawing Figures

CATHETER AND DRAIN TUBE RETAINER

BACKGROUND OF THE INVENTION

Various different forms of catheters and drain tubes are conventionally inserted into a patient's body and must remain therein for indeterminant lengths of time. However, movement of a patient within a bed and disturbance of the patient by nurses or other hospital personnel may cause a catheter or drain tube to be shifted longitudinally relative to the site through which the catheter or tube enters the patient's body. Although a catheter or drain tube may be taped in position, it is sometimes necessary to temporarily remove and subsequently re-install a catheter or drain tube. This of course would result in the re-installed catheter or drain tube having to be re-taped in position and the re-taping as well as the initial taping of a catheter or drain tube in place can cause considerable discomfort to the patient. Accordingly, a need exists for structure by which a catheter or drain tube may be frictionally retained in position against longitudinal displacement relative to the associated exit site and wherein that structure may be anchored to a patient adjacent the exit site in a manner which does not cause skin discomfort.

Examples of various different forms of positioners or anchor structures including some of the general structural and operational features of the instant invention are disclosed in U.S. Pat. Nos. 1,998,225, 2,133,130, 2,898,917, 3,893,446 and 4,040,428. However, these previously known devices are either not as efficient as or more cumbersome, complex and more expensive than the instant invention.

BRIEF DESCRIPTION OF THE INVENTION

The catheter and drain tube retainer of the instant invention comprises a simple peripheral frame body of relatively great thickness and including pressure sensitive adhesive on one side thereof whereby the frame body may be adhesively secured to the outer surface of a patient's skin surrounding the exit site of a catheter or drain tube. The frame body includes a membrane extending there across constructed of resilient shape retentive material and the membrane includes a central opening formed therein and radial slots extending outwardly from the opening. Those portions of the membrane defined between adjacent slots form generally triangular tongue portions whose free ends surround the central opening in the membrane. A catheter or drain tube of an outside diameter greater than the diameter of the opening may project through the latter in a manner laterally deflecting the free ends of the tongue portions of the membrane and those laterally directed tongue portions of the membrane are laterally deflected by the catheter or drain tube and frictionally grip the latter to resist longitudinal displacement of the catheter or drain tube.

This main object of this invention is to provide a catheter and drain tube positioner which may be used in conjunction with a catheter or drain tube at an exit site on a patient's skin to prevent longitudinal displacement of the catheter or drain tube through the exit site.

Another object of this invention is to provide a retainer or positioner in accordance with the preceding object and constructed in a manner whereby it may be used on numerous different portions of a patient's body.

Still another object of this invention is to provide a retainer or positioner which may be secured in position on a patient's body about the exit site of a catheter or drain tube through the utilization of pressure sensitive adhesive specifically designed not to cause skin irritation.

Another very important object of this invention is to provide a positioner or retainer which may be used in conjunction with catheters and drain tubes of different diameters.

A final object of this invention to be specifically enumerated herein is to provide a catheter or drain tube retainer in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF THE INVENTION

Figure 1:
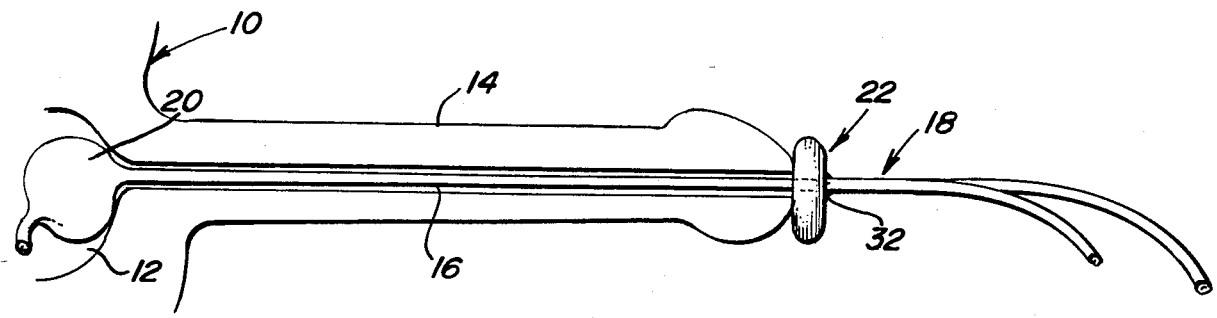
FIG. 1 is a fragmentary vertical sectional view illustrating the retainer of the instant invention in an operative association with a bladder catheter of a male patient.
Figure 2:
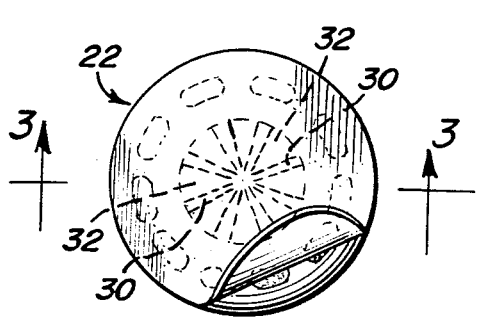
FIG. 2 is a face view of the retainer with the protective sheet overlying the pressure sensitive adhesive partially removed.
Figure 3:
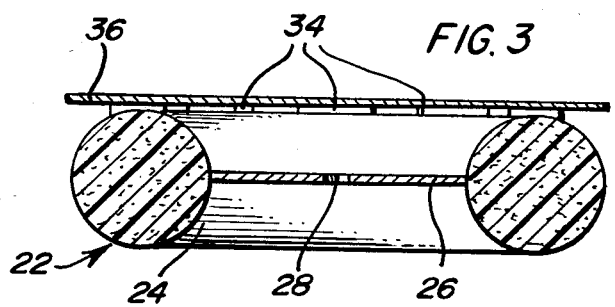
FIG. 3 is an enlarged sectional view taken substantially upon the plane indicated by the section line 3—3 of FIG. 2.

Referring now more specifically to the drawings the numeral 10 generally designates a male body including a bladder 12 and male organ 14 through which the urethra 16 extends into the bladder 12. A balloon type catheter is referred to in general by the reference numeral 18 and extends through the urethra 16 and has its balloon portion 20 inflated within the bladder 12.

The body or tube of the urethra 18 exits from the body through the free end of the organ 14 and is held against longitudinal shifting relative to the exit site by the retainer or positioner of the instant invention referred to in general by the reference numeral 22.

The retainer or positioner 22 defines a body constructed of shape retentive and resilient material and including a peripheral frame 24 extending about the body. In addition, the body also includes a membrane 26 extending there across.

The peripheral frame 24 is circular in plane and also circular in radial cross section. The frame 24 is relatively axially thick while the membrane 26 is relatively thin in comparison to the axial thickness of the frame 24. Further, the membrane 26 is disposed on the medial plane of the frame 24 spaced equally inwardly from the axial ends of the frame 24.

The central portion of the membrane 26 includes an opening 26 formed therethrough and the membrane 26 includes radial slots 30 formed therein extending outwardly from the opening 28 and defining generally triangular tongue portions 32 of the membrane 26 between adjacent pairs of slots 30. Inasmuch as the tongue portions 32 are constructed of shape retentive and resilient material, they may be laterally deflected outwardly of the medial plane of the membrane 26.

The catheter extends through the opening 28 and is of a diameter greater than the diameter of the opening 28 and thus laterally deflects the inner end portions of the tongue portions 32 in the manner illustrated in FIG. 1 of the drawings whereby the free inner ends of the tongue portions 32 frictionally grip the catheter 18 for frictionally retaining the latter in position relative to the organ 14 against longitudinal displacement relative thereto.

One axial end face of the frame 24 includes peripherally spaced amounts of pressure sensitive adhesive 34 thereon and the adhesive equipped axial end of the frame 24 is provided with a flexible adhesive protective sheet 36 which may be readily peeled from engagement with the adhesive 34 when it is desired to use the positioner or retainer 22. The protective sheet 36 is first removed and the catheter 18 has one end thereof inserted through the opening 28. Thereafter, the cathether may be inserted to the position illustrated in FIG. 1 of the drawings and the positioner 22 may thereafter be slid longitudinally of the outer free end of the catheter 18 toward a position with the adhesive equipped axial end of the positioner 22 engaging the outer skin portions of the organ 14 surrounding the exit site of the catheter 18. In this manner, the positioner 22 is adhesively secured in position relative to the free end of the organ 14 and frictionally grips the catheter 18 in order to resist longitudinal displacement of the catheter 18 relative to the exit site.

Figure 4:
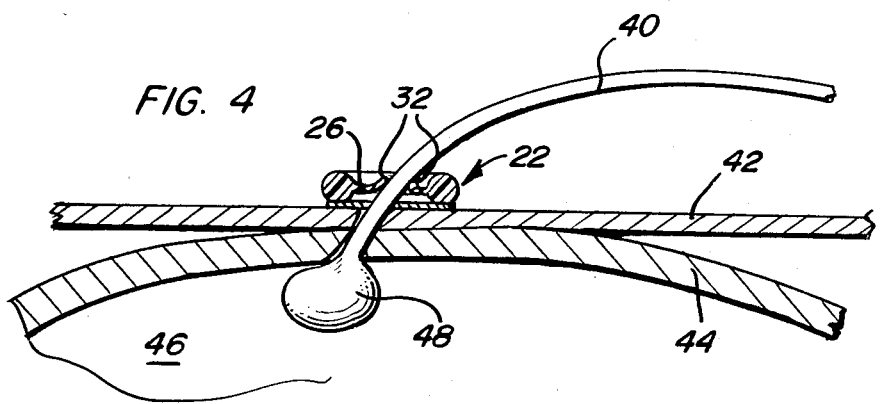
FIG. 4 is a fragmentary sectional view illustrating the manner in which the positioner may be used in conjuction with a balloon type catheter or drain extending through a patient's abdominal wall.

With attention now invited more specifically to FIG. 4 of the drawings, a second positioner 22 is illustrated in operative association with a drain tube 40 which has been inserted through the abdominal skin layer 42 and the abdominal wall 44 and into the abdominal cavity 46. The drain tube 40 includes an inflatable balloon portion 48 on the inner end thereof for preventing outward shifting of the drain tube 40 and the tuve 40 extends through the positioner 22 while the positioner 22 is adhesively attached to the outer skin layer 42. Thus, the drain tube 40 is frictionally held in position against longitudinal displacement through the exit site.

The adhesive 34 in some situations could be replaced by other attaching means such as a Velcro or other similar material ring attached to the frame 24. In such case, a more or less semi-permanent ring of a matching Velcro panel could be adhesively secured to the exterior skin surface about the exit site. Such a more permanent anchoring for the frame 24 would be used when a drain or catheter is to be used over extended periods of time.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is as follows:

1. A catheter and drain tube retainer, said retainer including a body having a peripheral frame of a first thickness and a membrane extending across the interior of the frame, said membrane being of a second thickness considerably less than the first thickness, said membrane including a central opening therein and generally radial slots formed therein extending outwardly from said opening toward said peripheral frame and defining generally triangular tongue protions of said membrane between adjacent slots and with the tapered apex portions of said tongue portions spaced about said opening, one side of said peripheral frame including attaching means for removably anchoring said frame in overlying relation to the outer surface of a body skin portion disposed about the exit site of a catheter or drain tube, said frame being circular in plan and generally circular in radial cross section.

2. The retainer of claim 1 wherein said membrane is generally centered between remote opposite side faces of said frame.

3. The retainer of claim 1 wherein said frame is constructed of shape retentive resilient foam material.

4. The retainer of claim 1 wherein said attaching means includes pressure sensitive adhesive means carried by said one side of said frame.

5. The retainer of claim 4 wherein said adhesive means is carried by said one side of said frame at points spaced apart circumferentially about said frame.

* * * * *